United States Patent [19]

Tax

[11] Patent Number: 4,914,089

[45] Date of Patent: Apr. 3, 1990

[54] PHARMACEUTICAL DOSAGE UNIT

[75] Inventor: Lambert J. W. M. Tax, Macharen, Netherlands

[73] Assignee: Akzo N.V., Arnhem, Netherlands

[21] Appl. No.: 215,838

[22] Filed: Jul. 6, 1988

[30] Foreign Application Priority Data

Jul. 6, 1987 [NL] Netherlands .................... 87.01586

[51] Int. Cl.$^4$ ............................................. A61K 31/56
[52] U.S. Cl. .................................................. 514/170
[58] Field of Search ........................................ 514/170

[56] References Cited

U.S. PATENT DOCUMENTS 3,502,772  3/1970  Ijzerman ............................. 514/170
4,378,356  3/1983  De Jager ............................. 514/170

FOREIGN PATENT DOCUMENTS 0136011  4/1985  European Pat. Off. .
0253670  1/1988  European Pat. Off. .

OTHER PUBLICATIONS

*Unlisted Drugs*, vol. 36, No. 6, Jun. 1984, p. 108, Item P, "Neophasic".

Primary Examiner—Douglas W. Robinson
Attorney, Agent, or Firm—William M. Blackstone; Donna Bobrowicz

[57] ABSTRACT

The invention relates to a pharmaceutical dosage unit for oral application for preventing or treating climacteric complaints.

11 Claims, No Drawings

PHARMACEUTICAL DOSAGE UNIT

The invention relates to a pharmaceutical dosage unit for oral application for preventing or treating climacteric complaints, which dosage unit contains an oestrogenic compound and a substance which is capable of inducing progestational activity, and to a pharmaceutical preparation which contains several of said dosage units.

Such dosage units and preparations are generally known. It has, however, been found that such preparations often have side effects such as an unfavourable effect on the so-called "high density lipid" (HDL) and triglyceride content and irregular abstraction haemorrhages.

It has now been found that a certain combination of $17\beta$-oestradiol and desogestrel do not exhibit said disadvantages. The abstraction haemorrhages are absent or regular so that the endometrium is not at risk (is excessively stimulated). In addition, metabolic parameters such as the HDL and triglyceride content remain at virtually the level such as is found without administering the preparation according to the present invention. As stated, the preparation according to the invention is extremely suitable for preventing or treating the climacteric syndrome and, in particular, vasomotor complaints including osteoporosis. $17\beta$-Oestradiol, which is attractive because it is one of the natural oestrogens, and desogestrel appear to supplement each other excellently. By administering a certain quantity of oestradiol bone loss is prevented and climacteric complaints are suppressed. Administration of a certain quantity of desogestrel during a certain period ensures that the side effects due to the administration of oestradiol are prevented without the administration of desogestrel giving rise to undesirable side effects (e.g. androgenic side effects).

The invention therefore relates to a pharmaceutical dosage unit for oral application for treating or preventing climacteric complaints, containing $17\beta$-oestradiol and desogestrel as active constituents and to a pharmaceutical preparation containing several of said dosage units.

A dosage unit contains 0.5–2.5 mg, and still more preferably, 0.75–2.25 mg of oestradiol and 100–300 μg, and still more preferably, 100–200 μg of desogestrel.

The simplest form of treatment of prevention of climacteric complaints is to administer one dosage unit per day without interruption. For this purpose, the dosage units which, preferably, each contain the same quantity of $17\beta$-ostradiol and each contain the same quantity of desogestrel, may be packaged in a simple manner without indicating the sequence of swallowing to be adopted. A suitable packaging form is, for example, a small bottle or small tube. In this case, the preparation contains no other dosage units than those according to the present invention.

If a periodical abstraction haemorrhage, for example after 1, 2 or 3 months, is preferred, use may be made of a pharmaceutical preparation which consists of at least two phases, the first phase comprising at least 11 and preferably 11–100, and still more preferably, 11–15 dosage units containing $17\beta$-oestradiol and the second phase 11–15 dosage units containing $17\beta$-oestradiol and desogestrel. Preferably, the preparation contains two or three phases.

If the preparation comprises two phases, both phases consists more preferably of 13–15 and still more preferably of 14 consecutive dosage units. If the preparation comprises three phases, the first and second phase consist preferably of 11–13, and still more preferably, of 12 consecutive dosage units.

The third phase, if present, consists of a period in which no dosage units are taken or of placebo's. Preferably, the period lasts 2–6 days and, still more preferably, 4 days, or the number of placebo's is 2–6 and, still more preferably, 4. The use of placebo's is preferred with a view to the convenience of the preparation for the user.

Although the presence of active constituents other than $17\beta$-oestradiol and desogestrel in the dosage units and preparation according to the present invention is not excluded, dosage units containing $17\beta$-oestradiol and desogestrel exclusively are preferred. In the case of two-phase and three-phase preparations, the quantity of $17\beta$-oestradiol and desogestrel may also vary over the different dosage units, but the preference is for the same quantity of $17\beta$-oestradiol and desogestrel for each dosage unit. During the period of administration, one dosage unit is administered daily, the sequence being determined by the manner in which the dosage units are arranged in the packaging of the preparation.

When mention is made of dosage units in the description (with the exception of the examples), these are understood to mean oral dosage units such as tablets, pills, capsules, dragees and granules. The oral dosage units are produced by mixing the desired quantities of desogestrel and oestradiol with the usual pharmaceutically acceptable auxiliary substances such as fillers, binders, colouring agents, flavourings and lubricants, and converting the mixture into the form of a pharmaceutical moulding or filling capsules therewith. A practical dosage form is the soft gelatin capsule.

It may be advisable to distinguish the placebo's and the dosage units mutually from each other in the different phases by a different design and/or colour.

Daily indications indicating the sequence in which the dosage units have to be taken are preferably provided on the packagings in which the two- and three-phase preparation according to the invention is packaged. The preparation may be packaged in a tube or a small box or in a so-called strip packaging. In the case of a small box, which may have a circular, rectangular or some other shape, the dosage units are separately confined therein, usually around the circumference of the small box, an optionally movable series of daily indications being provided on the small box corresponding to the days on which each of the dosage units has to be taken.

Another practical form of packaging is the so-called strip packaging or blister packaging in which each dosage unit is confined in a separate compartment and daily indications or other indications which specify the sequence in which the dosage units should be taken are provided on the strip or the packaging.

The invention is explained on the basis of the following examples.

EXAMPLE 1

Tablets containing the quantities of $17\beta$-oestradiol and desogestrel shown in Table 1 below and 0.080 mg of dl-α-tocopherol, 4.000 mg of potato starch, 0.600 mg of colloidal silicon dioxide, 0.200 mg of magnesium stearate, 2.200 mg of polyvinylpyrrolidone and sufficient lactose for the tablets to weigh a total of 80.000 mg were prepared by mixing a solution of desogstrel and tocopherol in acetone with a mixture of oestradiol, polyvinylpyrrolidone and lactose, mixing the granular material with starch after drying, colloidal silicon dioxide and magnesium stearate, and by moulding tablets from the composition thus formed.

TABLE 1

| Table | 1 | 2 | 3 | 4 | 5 | 6 | 7 | 8 |
|---|---|---|---|---|---|---|---|---|
| 17β-oestradiol (mg) | 1.500 | 1.250 | 2.000 | 2.000 | 1.000 | 1.000 | 1.500 | 0 |
| desogestrel (mg) | 0.150 | 0.150 | 0.100 | 0.150 | 0.150 | 0 | 0 | 0 |

EXAMPLE 2

Composition of pharmaceutical preparations containing the tablets prepared in Example 1.

TABLE 2

| Pharmaceutical preparation | 1 | 2 | 3 | 4 | 5 |
|---|---|---|---|---|---|
| 1st phase (number of a particular tablet) | 12 × tablet 7 | 14 × tablet 7 | 70 × tablet 6 | 12 × tablet 6 | 60 × tablet 5 |
| 2nd phase (as above) | 12 × tablet 1 | 14 × tablet 1 | 14 × tablet 5 | 12 × tablet 7 | — |
| 3rd phase (as above) | 4 × tablet 8 | — | — | 4 × nothing | — |

"—" denotes not applicable
"nothing" denotes that the third phase consists of a period in which nothing is taken.

I claim:

1. Pharmaceutical composition for oral administration for treating or preventing climacteric complaints, comprising 17β-oestradiol and desogestrel in the weight ratio, respectively, of from 25:1 to 25:15.

2. Pharmaceutical composition for oral administration for treating or preventing osteoporosis, comprising 17β-oestradiol and desogestrel in the weight ratio, respectively, of from 25:1 to 25:15.

3. Pharmaceutical composition as recited in claim 1 or 2, in the form of a single day dosage unit comprising 0.5-2.5 mg of 17β-oestradiol and 100-300 μg of desogestrel.

4. Pharmaceutical preparation comprising a plurality of single day dosage units according to claim 3.

5. Pharmaceutical preparation according to claim 4, consisting of single day dosage units according to claim 3.

6. Pharmaceutical preparation comprising at least 22 single day dosage units in a particular sequence in at least two phases, of which the first comprises at least 11 consecutive single day dosage units and the second comprises 11-15 consecutive single day dosage units, each dosage unit of the first phase containing 0.5-2.5 mg of 17β-oestradiol as the sole active constituent and each dosage unit of the second phase being a dosage unit according to claim 3.

7. Pharmaceutical preparation according to claim 6, wherein the number of single day dosage units is 22-30 and the first phase comprises 11-15 consecutive single day dosage units.

8. Pharmaceutical preparation according to claim 7, wherein the preparation consists of two phases, each containing 14 dosage units.

9. Pharmaceutical preparation according to claim 6, wherein the first and the second phase each contain 12 single day dosage units and the preparation also comprises a third phase which consists of 4 placebo dosage units containing no 17β-oestradiol and no desogestrel.

10. Pharmaceutical preparation according to claim 6, wherein the quantity of 17β-oestradiol in each dosage unit containing 17β-oestradiol is the same.

11. Pharmaceutical preparation according to claim 4, wherein the quantity of desogestrel in each dosage unit containing desogestrel is the same.

* * * * *